United States Patent
Kaus et al.

[11] Patent Number: 5,890,703
[45] Date of Patent: Apr. 6, 1999

[54] DEVICE FOR HUMIDIFYING THE USEFUL SPACE OF A CLIMATIC CABINET

[75] Inventors: Thomas Kaus, Langenselbold; Stefan Ferger, Ranstadt; Karl-Heinz Hessler; Hubert Heeg, both of Mömbris, all of Germany

[73] Assignee: Heraeus Instruments GmbH & Co. KG, Hanau, Germany

[21] Appl. No.: 858,237

[22] Filed: May 19, 1997

[30] Foreign Application Priority Data

May 22, 1996 [DE] Germany .................. 196 20 507.7

[51] Int. Cl.⁶ .................................................. B01F 3/04
[52] U.S. Cl. ................. 261/101; 261/104; 261/DIG. 4
[58] Field of Search .................. 261/101, 104, 261/DIG. 4

[56] References Cited

U.S. PATENT DOCUMENTS

| | | | |
|---|---|---|---|
| 1,621,766 | 3/1927 | Bulmer | 261/101 |
| 2,835,184 | 5/1958 | Leatherman | 261/101 |
| 3,788,545 | 1/1974 | Budd et al. | 261/104 |
| 4,614,299 | 9/1986 | Van Loveren et al. | |
| 4,622,049 | 11/1986 | Abernathy et al. | |
| 4,861,523 | 8/1989 | Beran | 261/104 |
| 4,921,642 | 5/1990 | LaTorraca | |
| 4,961,493 | 10/1990 | Kaihatsu | |
| 5,318,731 | 6/1994 | Yokoya et al. | 261/101 |
| 5,389,311 | 2/1995 | Hetzel | 261/104 |
| 5,480,591 | 1/1996 | Lagneaux et al. | 261/104 |
| 5,595,690 | 1/1997 | Filburn et al. | 261/104 |

FOREIGN PATENT DOCUMENTS

| | | | |
|---|---|---|---|
| 581462 | 2/1994 | European Pat. Off. | |
| 36 41 821 | 6/1988 | Germany | |
| 2-208430 | 8/1990 | Japan | 261/104 |
| 7-4701 | 10/1995 | Japan | |
| 2 223 694 | 4/1990 | United Kingdom | 261/104 |
| 94/29650 | 12/1994 | WIPO | |

*Primary Examiner*—C. Scott Bushey
*Attorney, Agent, or Firm*—Frishauf, Holtz, Goodman, Langer & Chick, P.C.

[57] ABSTRACT

A device for humidifying the useful space of a climatic chamber, the humidifying device having a flexible bag which defines water-holding reservoir defined by watertight walls. The flexible bag can be refilled through a closure. The flexible bag is at least partly made of a water-vapor-permeable material, such as a copolymer of tetrafluoroethylene and hexafluoropropylene, or polypropylene. The efficiency can be improved compared with conventional open humidifying systems by appropriately structuring the surface of at least the water-vapor-permeable part of the humidifying bag, for example, by providing tufts. To impart form stabilization to the bag, its opposite faces can be joined to each other through the inside of the bag by heat-sealing or stitching.

17 Claims, 3 Drawing Sheets

DEVICE FOR HUMIDIFYING THE USEFUL SPACE OF A CLIMATIC CABINET

BACKGROUND OF THE INVENTION

1. Field of the Invention

The present invention relates to a device for humidifying the useful space of a climatic chamber. More particularly, the humidifying device of the present invention having a completely closed water-holding reservoir defined by watertight walls, at least part of the reservoir being made of material that is permeable to water vapor, but is impervious to liquid water.

2. Background Information

Climatic cabinets such as incubators or aerators/incubators of the various models described, for example, in brochures of Heraeus Instruments GmbH are usually equipped with an open trough containing a water supply for continuously humidifying the atmosphere of the useful volume to a relative humidity of about 95%. At temperatures such as 37° C., environmental conditions as close as possible to natural conditions are simulated for the cell and tissue cultures growing "in vitro" in such incubators. Contamination by fungi, bacteria or Mycoplasma species must be absolutely prevented, since it can destroy valuable cultures or lead to false study results. Open humidifying devices therefore always represent a potential source of contamination, which can be kept under control only by elaborate cleaning procedures. Moreover, water spills that must then be dried up again can easily occur when the water reservoir is being removed or filled. The walls of the useful space of a climatic cabinet themselves must be kept as dry as possible, in order to exclude the possibility of accumulations of dirt and contamination.

A certain useful volume corresponding to its dimensions is reserved for the usual humidifying device with an open water reservoir. Such water reservoirs cannot be placed conveniently in positions other than provided by design. In the individual case, this may mean that the cell cultures are not optimally humidified. Additional water reservoirs can certainly be placed in the climatic cabinet or incubator, but they then reduce the usable volume available to the culture vessels. Furthermore, the free water surface is naturally limited by the construction of the reservoir. On the other hand, a large surface area for evaporation of the water is desirable in order to increase the efficiency of the humidifying device.

A trough-shaped reservoir with an opening spanned by a water-vapor-permeable membrane is also known from DE 36 41 821 A 1. In this case the reservoir functions as a moisture source for a measuring technique for testing the water-vapor permeability of materials. The measurements are performed in a climatic cabinet. As in the cited prior art, this humidifying device also suffers from the disadvantages of a trough that allows little variation in use thereof, occupies a relatively large space, provides only a small surface area for releasing water vapor and has elaborate means for closing and fixing the membrane.

U.S. Pat. No. 4,622,049 discloses a two-compartment test device with a supply reservoir of saturated aqueous saline solution in the lower compartment. In this case also the humidifying device consists of a fixed trough, wherein a small part of that surface of the said trough which faces the second, upper compartment is provided with a water-vapor-permeable membrane or with glass wool. The dimensions of the upper and lower compartments are matched such that they can be coupled form-fittingly together, and so the device can be regarded as a total system. Thus this device also merely represents a further variant of the already described general prior art (fixed water reservoir/trough).

From WO 94/29650 there is also known an air-humidifying system for climatic installations, which system contains one section with water-vapor-permeable membranes. The membranes are clamped in a fixed frame, and the water is passed between two membranes designed as filters for microbes, particles and dissolved salts. The water-supply reservoir is connected separately and via a piping system with the membrane frame. The section constructed as the membrane cell is bounded by membranes on two sides. The frame and the membrane-clamping means impart a rigid form to the overall construction, and so here also a fixed reservoir with the known disadvantages is obtained.

A so-called scent bag is known from U.S. Pat. No. 4,961,493. In this case a substance containing a liquid or gel-like fragrance or perfume is held in a gas-permeable, but liquid-tight bag. The bag cannot be refilled without destroying it, and its purpose is to freshen the air, at a temperature of about 25° C., in living rooms or passenger vehicles, where strict requirements of sterility or autoclavability are not a concern. The container is designed as a disposable article, which loses its function as a source of gaseous fragrances after some time and, since it cannot be refilled, must be replaced by a new fragrance bag. This bag is completely unsuitable for use in well defined atmospheres such as are necessary in climatic cabinets.

SUMMARY OF THE INVENTION

In contrast to the above, the object of the invention is to provide, for humidifying climatic cabinets, a device that minimizes the risk of contamination, operates with high efficiency and is suitable for different conditions in the useful space.

This object is achieved according to the invention by a reservoir that is constructed as a flexible bag that can be refilled through a closure, at least the water-vapor-permeable part of the flexible bag having a surface area larger than that of a smooth unstructured surface. The flexible bag is preferably filled outside the climatic cabinet, and so there is no concern about potential dirt accumulation in or on the climatic cabinet even in the event of spillage. The bag has a tight closure that is easy to open and close. The bag can be constructed to have a cap, stopper or screw-type closure, or as a combination thereof. The porosity of the water-vapor-permeable membrane is adapted such that the necessary relative humidity is reached in a short time, just as with the known open humidifying devices. This is achieved by making the bag from a water-vapor-permeable membrane with a structured surface, for example, a tufted surface. In this way, the area from which the water vapor emerges is maximized relative to the quantity of water to be evaporated.

A further increase in evaporation surface area is achieved by additional stitched seams. These also impart form stabilization to the bag, enabling it to be placed or suspended in flat, mattress-like form in the useful space of the climatic cabinet. Such form stabilization can be achieved by joining (stitching, heat-sealing, bonding or similar method) opposite faces of the bag through the inside of the bag. In addition, a stiff plastic liner can be inserted and fixed in the inside of the bag, especially by stitched points, to contribute to form stabilization. By virtue of the diverse forms that can be achieved with this humidifying device, it is possible to use whichever form is optimal for the particular geometric conditions in the useful space of the climatic chamber.

For example, a cell culture may require high humidity rapidly and continuously. In the prior art, this means a large water reservoir with the largest possible open evaporation surface, which once again must be regarded as a contamination risk the longer it is in operation. Aside from this, such large-volume, open reservoirs necessitate a correspondingly large climatic cabinet. With the humidifying device according to the invention, however, a bag with small outer dimensions and relatively large capacity, achieved by suitable geometry and surface structuring, can be placed or suspended in a small climatic chamber or incubator, thus achieving greater humidification efficiency than in the conventional system.

"Modified Teflon" (a copolymer of tetrafluoroethylene and hexafluoropropylene) ("FEP") has proved advantageous as a water-vapor permeable, but liquid-tight material. This material can be easily processed by heat-sealing, stitching, embossing or similar techniques. Furthermore, the material is repeatedly resistant to exposure to high steam pressure at about 140° C., as is normally used in sterilizing autoclaves. Alternatively, polypropylene (PP) can also be used as reservoir material.

BRIEF DESCRIPTION OF THE DRAWINGS

Practical examples of the invention will be explained hereinbelow with reference to the drawings. It is understood, however, that the present invention is not limited to the precise arrangements and instrumentalities depicted in the drawings.

DETAILED DESCRIPTION OF THE INVENTION

Figure 1:
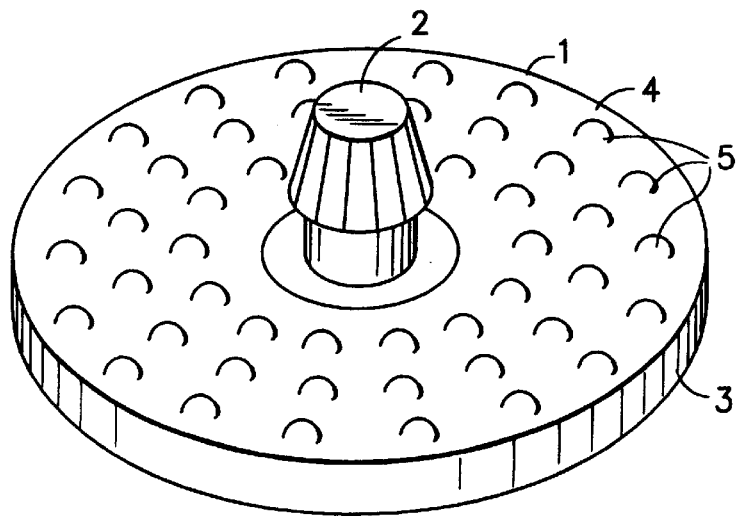
FIG. 1 is a perspective view of a simple humidifying bag of the present invention without stiffenings.

FIG. 1 shows a round bag 1, which has a screw-type closure 2 at the center of the top side. Other than this screw-type closure 2, the bag 1 does not have any stiffening elements, and so it assumes a balloon-like form when filled with water. If the bag is not filled to the maximum with water, it remains particularly flexible and thus adaptable to external forms such as imposed by the geometry of the useful space of the climatic cabinet or/and by the arrangement of culture vessels and/or by additional support elements therein.

The round bag 1 can be made completely from water-vapor-permeable but liquid-tight material. It may also be appropriate to make the bearing face 3 of the round bag 1 from a flexible or stiffened material that is impervious to both water vapor and liquid, and which is heat-sealed together with the water-vapor-permeable but liquid-tight material according to the invention and constituting the upper part 4 of the round bag 1. In this embodiment, the water-vapor-permeable upper part 4 of the round bag 1 is also provided with upwardly directed tufts 5 to increase the surface area.

Figure 2:
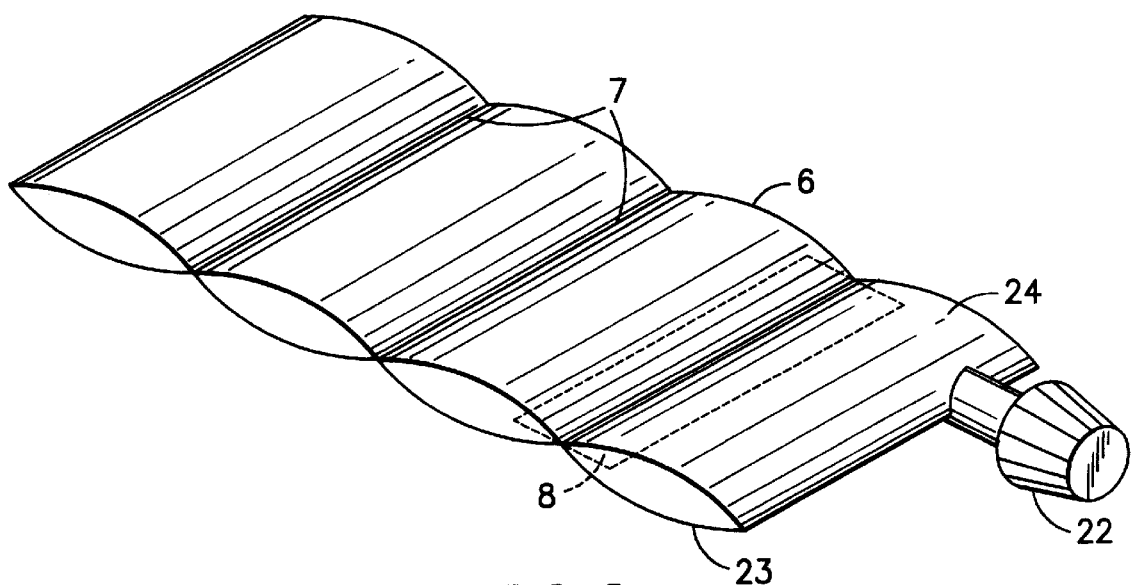
FIG. 2 is a perspective view of a humidifying bag of the present invention with linear, continuous stitched seams.

FIG. 2 shows a rectangular, flat humidifying bag 6, which is given a mattress-like form by linear continuous stitched seams 7. The stitched seams 7 join the upper and lower sides 24, 23, respectively, of the rectangular, flat humidifying bag 6 together, and thereby give it a stiffened form. At one corner of the rectangular, flat humidifying bag 6 there is attached a cap-type closure 22 for filling the rectangular, flat humidifying bag 6 with water. As in the first example, the rectangular, flat humidifying bag 6 can be made completely of a material that is permeable to water vapor, but is impervious to liquid water. Once again, however, it is possible for only the upper side 24 to be made of such material. If the stiffening due to the stitched seams 7 is not sufficient alone, the stitches 7 can be additionally backed with an intermediate layer 8, e.g., of stiff plastic film.

Figure 3:
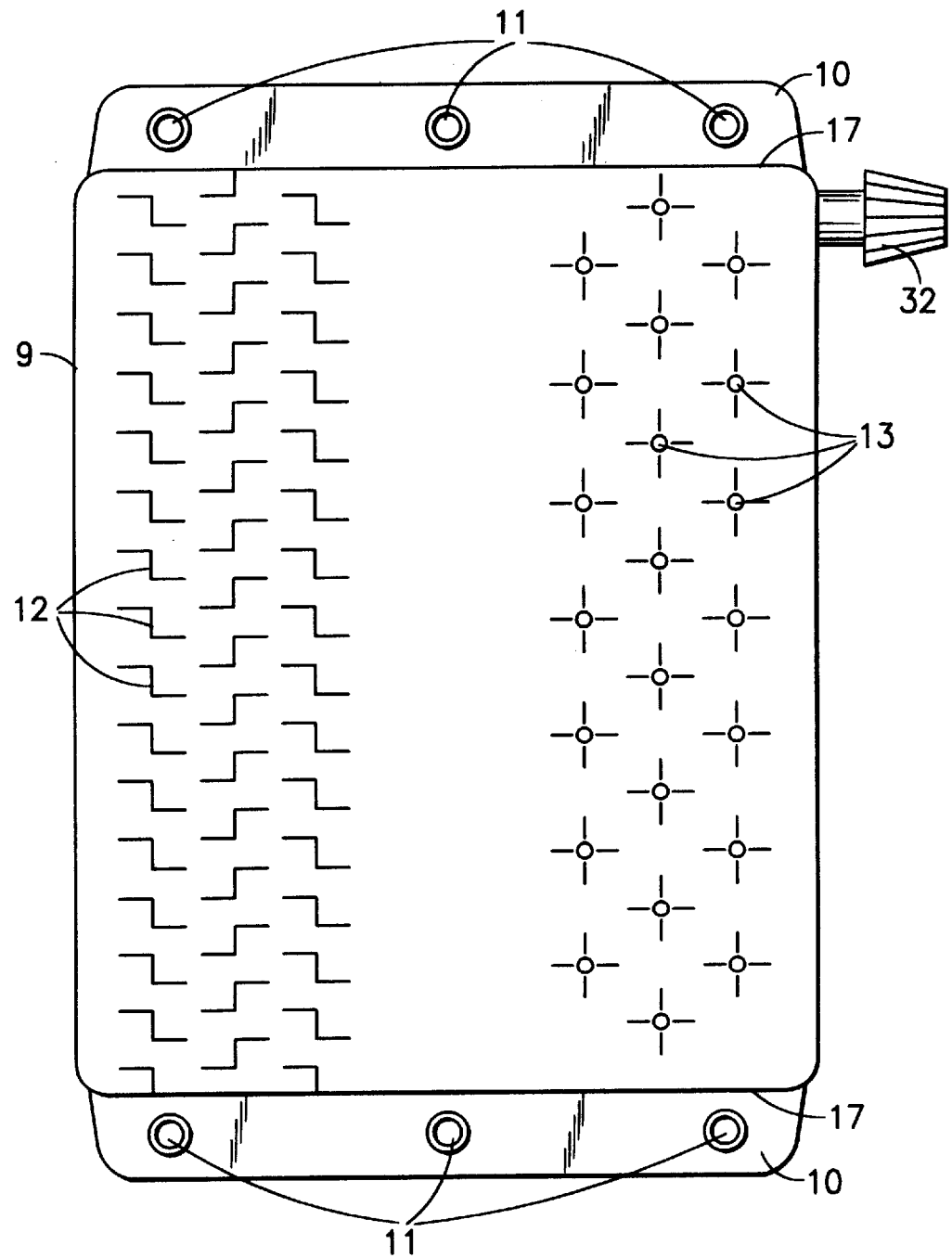
FIG. 3 is an elevation view of a humidifying bag of the present invention with suspension eyes and linear stitches or stitched points.

FIG. 3 shows a practical example of a suspendable humidifying bag 9. At each of two ends of the basically rectangular bag 9, a border portion 10 of bag material projects by a few centimeters beyond the bag 9. A plurality of eyes 11 for suspending the bag is provided in this section. The projecting border 10 is separated from the fillable bag 9 by a stitched or heat-sealed seam 17. The bag 9 itself is subdivided into compartments by stitched seams 12 or by stitched points 13 which, as already explained, serve as form stabilization.

The bag 9 provided as a suspended humidifying device is comprised entirely of water-vapor-permeable but liquid-tight material such as "modified Teflon" (FEP). For refilling, the bag is equipped with a closure 32 with a closure cap.

Figure 4:
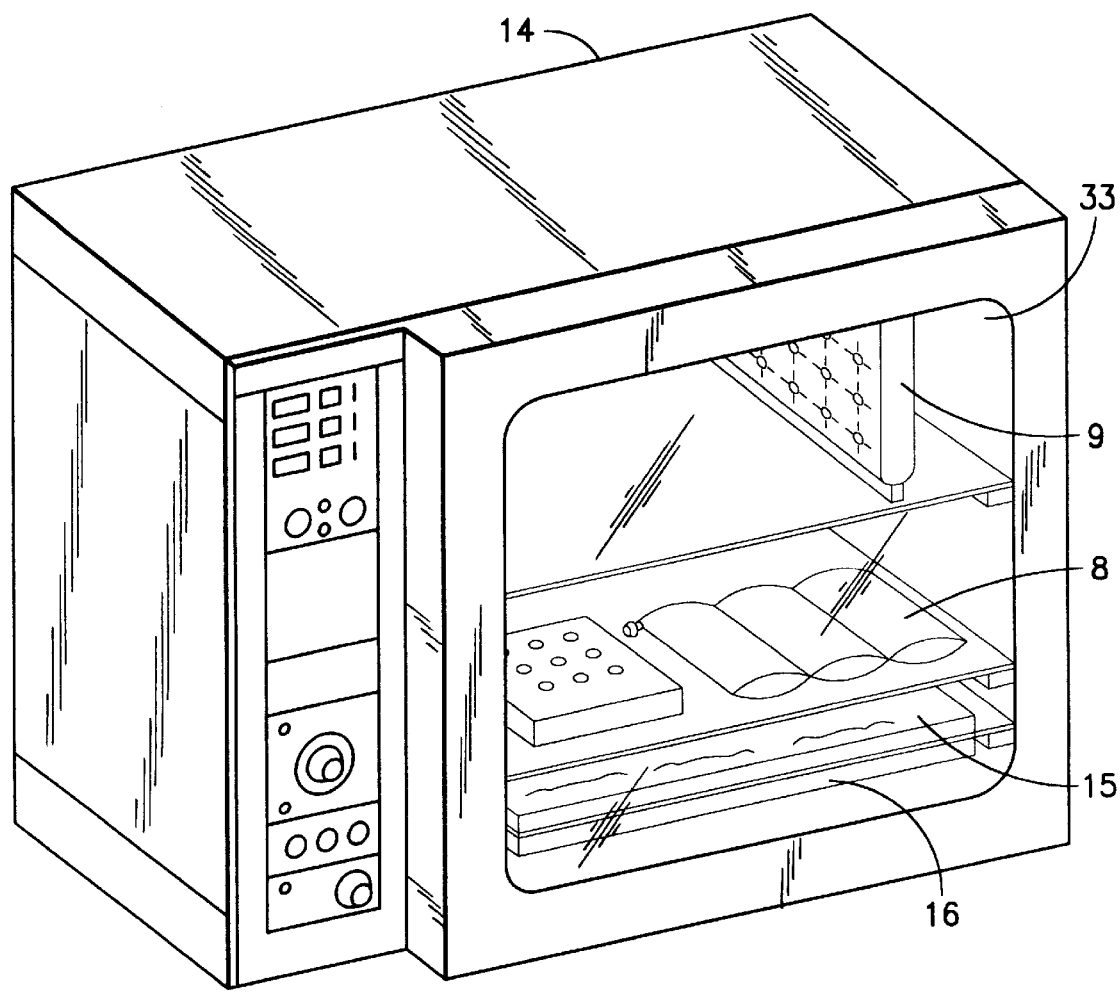
FIG. 4 is a perspective view which shows the humidifying device of the present invention in the useful space of a climatic chamber.

FIG. 4 shows an arrangement of the humidifying device in the useful space 33 of a climatic chamber 14. The practical examples of a flat, mattress-like bag 6 and of a suspendable bag 9, described in detail with reference to FIGS. 2 and 3, are disposed at different positions in the useful space 33. In a trough 16 in the bottom region of the useful space 33 there can be seen a simple humidifying bag 15, which by virtue of its flexible form adapts to the form of the trough 16.

It will be appreciated that the instant specification is set forth by way of illustration and not limitation, and that various modifications and changes may be made without departing from the spirit and scope of the present invention.

What is claimed is:

1. A device for humidifying the useful space of a climatic chamber, comprising:

a flexible bag which defines a completely closed water-holding reservoir having watertight walls, at least part of said reservoir being made of material that is permeable to water vapor, but is impervious to liquid water, a closure attached to the flexible bag for refilling the flexible bag, at least the water-vapor-permeable part of the flexible bag having a surface area larger than that of a smooth unstructured surface, and a stiff liner disposed inside the flexible bag, wherein the stiff liner is affixed to the flexible bag by stitched points.

2. The humidifying device according to claim 1, wherein the water-vapor permeable part of the bag is disposed on an outer surface of the bag.

3. The humidifying device according to claim 2, wherein said bag has opposite faces which are joined to each other through the inside of the bag.

4. The humidifying device according to claim 3, wherein the opposite faces of said bag are joined by stitching.

5. The humidifying device according to claim 1, wherein said reservoir is made of a copolymer of tetrafluoroethylene and hexafluoropropylene.

6. The humidifying device according to claim 1, wherein said bag has a tufted outer surface.

7. The humidifying device according to claim 6, wherein said reservoir is made of polypropylene.

8. The humidifying device according to claim 1, wherein the closure is a screw closure.

9. The humidifying device according to claim 1, wherein the bag is made entirely of the material that is permeable to water vapor, but is impervious to liquid water.

10. The humidifying device according to claim 1, wherein the bag is made entirely of a copolymer of tetrafluoroethylene and hexafluoropropylene.

11. The humidifying device according to claim 1, wherein an upper side of the bag is made of a copolymer of tetrafluoroethylene and hexafluoropropylene.

12. The humidifying device according to claim 1, wherein the bag is divided into a plurality of compartments by stitched seams or stitched points.

13. The humidifying device according to claim 1, further comprising a border portion disposed adjacent to at least one outer surface, said border portion containing at least one hole with an eye for suspending said bag.

14. The humidifying device according to claim 1, wherein said bag has opposite faces which are joined to each other through the inside of the bag.

15. The humidifying device according to claim 14, wherein said reservoir is made of a copolymer of tetrafluoroethylene and hexafluoropropylene, or is made of polypropylene.

16. The humidifying device according to claim 15, wherein said bag has a tufted outer surface.

17. The humidifying device according to claim 16, wherein the bag is divided into a plurality of compartments by stitched seams or stitched points.

* * * * *